United States Patent
Olek

(10) Patent No.: US 11,680,294 B2
(45) Date of Patent: Jun. 20, 2023

(54) AMPLICON REGION AS EPIGENETIC MARKER FOR THE IDENTIFICATION OF NON-CLASSICAL MONOCYTES

(71) Applicant: Precision for Medicine GmbH, Berlin (DE)

(72) Inventor: Sven Olek, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 101 days.

(21) Appl. No.: 16/758,992

(22) PCT Filed: Oct. 26, 2018

(86) PCT No.: PCT/EP2018/079406
§ 371 (c)(1),
(2) Date: Apr. 24, 2020

(87) PCT Pub. No.: WO2019/081707
PCT Pub. Date: May 2, 2019

(65) Prior Publication Data
US 2020/0340053 A1 Oct. 29, 2020

(30) Foreign Application Priority Data
Oct. 27, 2017 (DE) .......................... 102017125335.1

(51) Int. Cl.
*C12Q 1/68* (2018.01)
*C12Q 1/6881* (2018.01)

(52) U.S. Cl.
CPC ..... *C12Q 1/6881* (2013.01); *C12Q 2600/154* (2013.01)

(58) Field of Classification Search
None
See application file for complete search history.

(56) References Cited

FOREIGN PATENT DOCUMENTS

WO  WO 2012/162660 A2  11/2012
WO  WO 2014/170497 A2  10/2014
(Continued)

OTHER PUBLICATIONS

Feng (PNAS 2010 vol. 107 No. 19 pp. 8689-8694) (Year: 2010).*
(Continued)

*Primary Examiner* — Juliet C Switzer
(74) *Attorney, Agent, or Firm* — BakerHostetler

(57) ABSTRACT

The present invention relates to a method, in particular an in vitro method, for identifying non-classical monocytes, comprising analyzing the methylation status of at least one CpG position in the mammalian genomic region comprising an amplicon, wherein a demethylation or lack of methylation of said region is indicative for a non-classical monocyte, when compared to a classical monocyte or a non-monocyte cell. The analyses according to the invention can identify non-classical monocytes on an epigenetic level and distinguish them from all other cells in complex samples, such as, for example, other blood or immune cells. The present invention furthermore provides an improved method for quantifying non-classical monocytes, in particular in complex samples. The method can be performed without a step of purifying and/or enriching cells, preferably in whole blood and/or non-trypsinized tissue.

Figure 1:
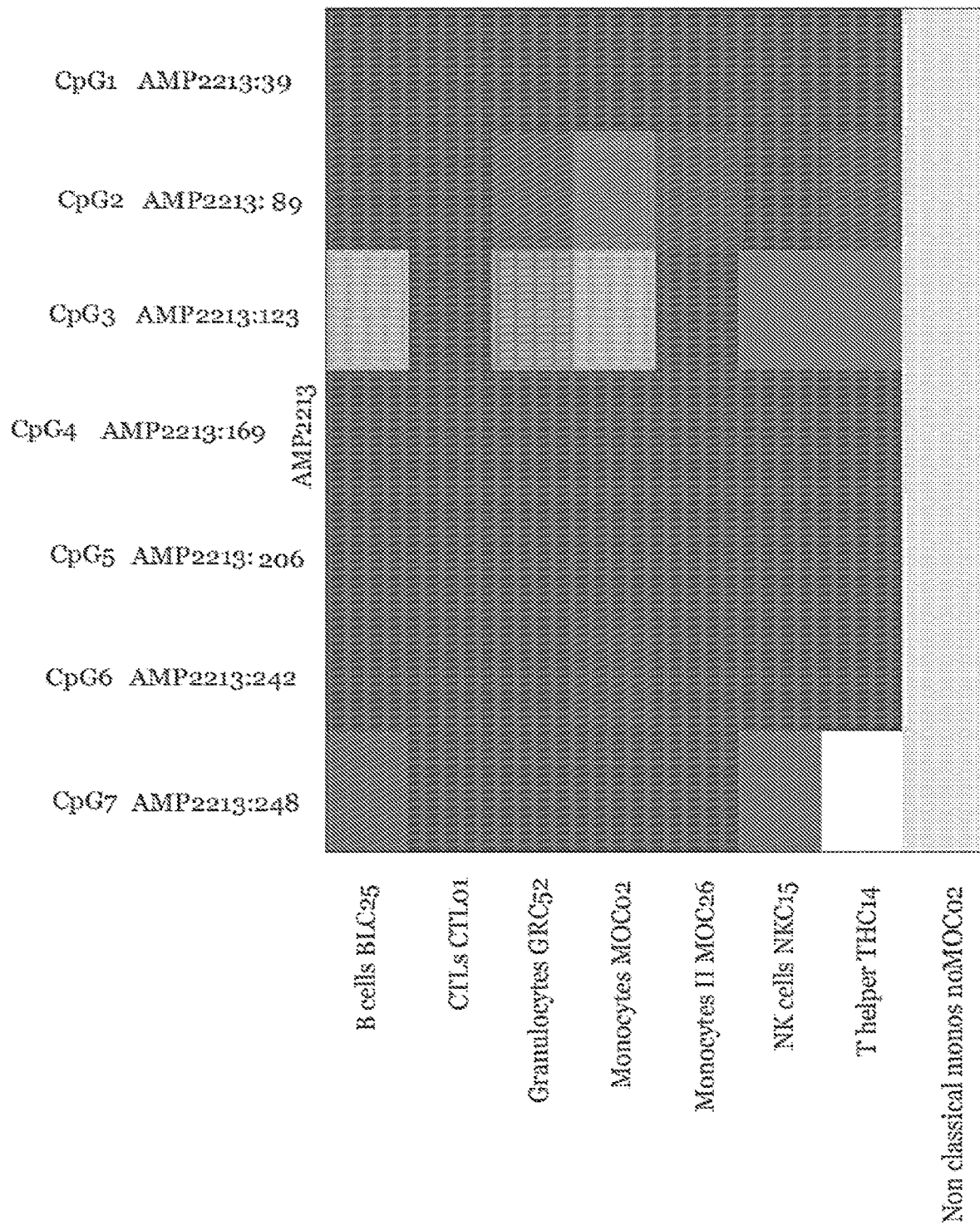

14 Claims, 2 Drawing Sheets
Specification includes a Sequence Listing.

(56) References Cited

FOREIGN PATENT DOCUMENTS

| | | | |
|---|---|---|---|
| WO | WO-2014170497 A2 * | 10/2014 | ........... C12Q 1/6851 |
| WO | WO 2017/050925 A1 | 3/2017 | |

OTHER PUBLICATIONS

GenBank Record having Accession AL355512, Human DNA sequence from clone RP11-525A16 on chromosome 10, complete sequence, published Dec. 13, 2012. 45 pages (obtained from https://www.ncbi.nlm.nih.gov/nuccore/al355512.22 on Jul. 14, 2022) (Year: 2012).*
Accomando et al., Quantitative reconstruction of leukocyte subsets using DNA methylation, Genome Biol. Mar. 5, 2014, 15(3).
Antequera and Bird, Number of CpG Islands and Genes in Human and Mouse, Proc Natl Academy of Science USA 90: 11995-9, 1993.
Booth, Michael J. et al., Quantitative Sequencing of 5-Methylcytosine and 5-Hydroxymethylcytosine at Single-Base Resolution, Science May 18, 2012, vol. 336, No. 6083, pp. 934-937.
Illingworth et al., A novel CPG island set identifies tissue-specific methylation at developmental gene loci, PLoS Biol Jan. 2008, 6(1): e22.
Jones and Laird, Cancer-Epigenetics Comes of Age, Nature Genetics 21: 163-167, 1999.
Kristensen and Hansen, PCR-Based Methods for Detecting Single-Locus DNA Methylation Biomarkers in Cancer Diagnostics, Prognostics, and Response to Treatment, Clinical Chemistry 55:8 1471-1483 (2009).
Laird, Peter W., The Power and the Promise of DNA Methylation Markers, Nature Reviews Cancer 3, pp. 253-266 (2003).
Zawada et al., DNA methylation profiling reveals differences in the 3 human monocyte subsets and identifies uremia to induce DNA methylation changes during differentiation, Epigenetics, Apr. 2, 2016, 11(4): 259-272.

* cited by examiner

SEQUENCE LISTING

<160> NUMBER OF SEQ ID NOS: 11

<210> SEQ ID NO 1
<211> LENGTH: 271
<212> TYPE: DNA
<213> ORGANISM: Homo sapiens

<400> SEQUENCE: 1

```
cccttcctct gactcagtgg aagggcagga gagtgccccg aggagctgcc cacatccctg    60
gctgagtgcc tcaccccag ggcctccacg aggagcagct tccacagggt gcctgtgggg   120
ctcgttcctc tggatgcttt tccctttgct gtgaatgcct ctggggcacg aatatatggc   180
ccttgggtct aggccttagg gcttccggtg accaggatag gaagtgttgc aggccctgcc   240
ccgagggcgg cgcattagct tttcccccac t                                  271
```

```
<210> SEQ ID NO 2
<211> LENGTH: 300
<212> TYPE: DNA
<213> ORGANISM: Homo sapiens

<400> SEQUENCE: 2
cccttcctct aactcaataa aaaaacaaaa aaatacccca aaaaactacc cacatcccta    60
actaaatacc tcaccccaa aacctccaca aaaacaact tccacaaaat acctataaaa    120
ctcattcctc taaatacttt tccctttact ataaatacct ctaaaacaca aatatataac   180
ccttaaatct aaaccttaaa acttccaata accaaaataa aaatattac aaaccctacc   240 ccaaaaacaa cacattaact tttcccccac tactttcatc tacccatctc accaaattcc   300
```

```
<210> SEQ ID NO 3
<211> LENGTH: 300
<212> TYPE: DNA
<213> ORGANISM: Homo sapiens

<400> SEQUENCE: 3
cccttcctct aactcaataa aaaaacaaaa aaatacccg aaaaactacc cacatcccta    60
actaaatacc tcaccccaa aacctccacg aaaacaact tccacaaaat acctataaaa    120
ctcgttcctc taaatacttt tcccttact ataaatacct ctaaaacacg aatatataac   180
ccttaaatct aaaccttaaa acttccgata accaaaataa aaatattac aaaccctacc   240 ccgaaaacga cgcattaact tttcccccac tactttcatc tacccatctc accaaattcc   300
```

```
<210> SEQ ID NO 4
<211> LENGTH: 22
<212> TYPE: DNA
<213> ORGANISM: Homo sapiens

<400> SEQUENCE: 4
cccttcctct aactcaataa aa                                            22
```

```
<210> SEQ ID NO 5
<211> LENGTH: 19
<212> TYPE: DNA
<213> ORGANISM: Homo sapiens

<400> SEQUENCE: 5
agtgggggaa aagttaatg                                                19
```

```
<210> SEQ ID NO 6
<211> LENGTH: 29
<212> TYPE: DNA
<213> ORGANISM: Homo sapiens

<400> SEQUENCE: 6
cccttaaatc taaaccttaa aacttccaa                                     29
```

```
<210> SEQ ID NO 7
<211> LENGTH: 24
```

```
<212> TYPE: DNA
<213> ORGANISM: Homo sapiens

<400> SEQUENCE: 7
tagtggggga aaagttaatg tgtt                                              24

<210> SEQ ID NO 8
<211> LENGTH: 25
<212> TYPE: DNA
<213> ORGANISM: Homo sapiens

<400> SEQUENCE: 8 acaaaccta ccccaaaaac aacac                                              25

<210> SEQ ID NO 9
<211> LENGTH: 28
<212> TYPE: DNA
<213> ORGANISM: Homo sapiens

<400> SEQUENCE: 9
ccttaaatct aaaccttaaa acttccga                                          28

<210> SEQ ID NO 10
<211> LENGTH: 22
<212> TYPE: DNA
<213> ORGANISM: Homo sapiens

<400> SEQUENCE: 10
gtggaggaaa agttaatgcg tc                                                22

<210> SEQ ID NO 11
<211> LENGTH: 24
<212> TYPE: DNA
<213> ORGANISM: Homo sapiens

<400> SEQUENCE: 11
caaaccctac cccgaaaacg acgc                                              24
```

AMPLICON REGION AS EPIGENETIC MARKER FOR THE IDENTIFICATION OF NON-CLASSICAL MONOCYTES

CROSS-REFERENCE TO RELATED APPLICATIONS

This application is a 35 U.S.C. § 371 national phase application of International Patent Application No. PCT/EP2018/079406, filed Oct. 26, 2018, which claims priority to German Patent Application No. 102017125335.1, filed Oct. 27, 2017, the entire disclosures of each of which are incorporated herein by reference in their entirety.

The Sequence Listing for this application is labeled "113828.000022 Sequence Listing.txt", which was created on Apr. 22, 2020 and is 3 Kilobytes. The entire content is incorporated herein by reference in its entirety.

The present invention relates to a method, in particular an in vitro method, for identifying non-classical monocytes, comprising analyzing the methylation status of at least one CpG position in the mammalian genomic region comprising an amplicon, wherein a demethylation or lack of methylation of said region is indicative for a non-classical monocyte, when compared to a classical monocyte or a non-monocyte cell. The analyses according to the invention can identify non-classical monocytes on an epigenetic level and distinguish them from all other cells in complex samples, such as, for example, other blood or immune cells. The present invention furthermore provides an improved method for quantifying non-classical monocytes, in particular in complex samples. The method can be performed without a step of purifying and/or enriching cells, preferably in whole blood and/or non-trypsinized tissue.

Furthermore, the present invention relates to a kit for performing the above methods as well as respective uses thereof. It is one aim of this invention to provide a novel, more robust means to quantitatively detect and measure non-classical monocytes of the blood within any solid organs or tissue or any other body fluid of a mammal.

BACKGROUND OF THE INVENTION

Monocytes are the largest type of white blood cells (leukocytes). They compose 2% to 10% of all leukocytes in the human body, and around half of them are stored in the spleen. Monocytes are part of the innate immune system of vertebrates including all mammals (humans included), birds, reptiles, and fish, and as such can influence the process of adaptive immunity. Monocytes can differentiate into macrophages and myeloid lineage dendritic cells to elicit an immune response. Monocytes play multiple roles in immune function. Such roles include: (1) replenishing resident macrophages under normal states, and (2) in response to inflammation signals, monocytes can migrate quickly to sites of infection in the tissues.

There are at least three types of monocytes in human blood, which differ in their expression of cell surface receptors. The "classical" monocyte is characterized by high level expression of the CD14 cell surface receptor (CD14++ CD16− monocyte). In contrast, "non-classical" monocytes express CD14 and additionally co-express the CD16 receptor. The "non-classical" monocytes can further be subdivided into monocytes that show low level expression of CD14 and high co-expression of CD16 (CD14+CD16++ monocyte). The "intermediate" monocytes express high levels of CD14 and low levels of CD16 (CD14++CD16+ monocytes).

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfite sequencing to map and quantify 5hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

WO 2012/162660 describes methods using DNA methylation arrays provided for identifying a cell or mixture of cells and for quantification of alterations in distribution of cells in blood or in tissues, and for diagnosing, prognosing and treating disease conditions, particularly cancer. The methods use fresh and archival samples.

Zawada et al. (in: Zawada et al. DNA methylation profiling reveals differences in the 3 human monocyte subsets and identifies uremia to induce DNA methylation changes during differentiation. Epigenetics. 2016 Apr. 2; 11(4):259-72. doi: 10.1080/15592294.2016.1158363. Epub 2016 Mar.

28) used next-generation Methyl-Sequencing to disclose differences within the DNA methylome of the different subsets of monocytes. They further described genes with differentially methylated promoter regions in monocytes, which are linked to different immunological processes. The genomic region within the 2213 amplicon is not mentioned.

Illingworth et al. (in Illingworth et al. A novel CpG island set identifies tissue-specific methylation at developmental gene loci. PLoS Biol. 2008 January; 6(1):e22. doi: 10.1371/journal.pbio.0060022) disclose variations within the methylation pattern of three different CpG islands in monocytes compared to granulocytes derived from blood samples. No indication of the 2213 amplicon is given.

Accomando et al. (in: Accomando et al. Quantitative reconstruction of leukocyte subsets using DNA methylation. Genome Biol. 2014 Mar. 5; 15(3)) disclose that cell lineage-specific DNA methylation patterns distinguish normal human leukocyte subsets and can be used to detect and quantify these subsets in peripheral blood. They used DNA methylation to simultaneously quantify multiple leukocyte subsets and to identify cell lineage-specific DNA methylation signatures that distinguish human T cells, B cells, NK cells, monocytes, eosinophils, basophils and neutrophils. The amplicon 2213 is not mentioned.

In view of the above, it is an object of the present invention to provide an improved and in particular robust method based on DNA-methylation analysis as a superior tool in order to more conveniently and reliably detect, identify, discriminate, and quantify non-classical monocytes.

The present invention solves the above object by providing a method for identifying non-classical monocytes in a sample, comprising analyzing the methylation status (bisulfate convertibility) of at least one CpG position in the mammalian (e.g. human) genomic region comprising the 2213 amplicon (AMP 2213) sequence, wherein preferably said region as analyzed is positioned based on/according to SEQ ID NO: 1, wherein a demethylation of said region is indicative for a non-classical monocyte, when compared to a classical monocyte or a non-monocyte cell.

The mammalian region within the 2213 amplicon has not been associated with a specific gene. In the context of the present invention, the region shall comprise the entire genomic region relating to and encoding for any gene within the 2213 amplicon. Thus, included are enhancer regions, promoter region(s), introns, exons, and non-coding regions (5'- and/or 3'-regions) that belong to any gene within the 2213 amplicon. Preferred is thus a method according to the present invention, wherein the at least one CpG position is present in a 5' region upstream from the transcription start, promoter region, a 5' or 3' untranslated region, exon, intron, exon/intron border and/or in a 3' region downstream of the transcriptional stop of any gene within the 2213 amplicon.

The present invention is further based on the surprising identification of the 2213 amplicon as specific epigenetic marker by the inventors, allowing the identification of non-classical monocytes as well as the clinical routine application of said analysis.

In the context of the present invention, the genomic region within the 2213 amplicon, in particular according to SEQ ID NO: 1 allows the identification of non-classical monocytes.

Surprisingly, the discriminatory pattern of bisulfite convertible and non-convertible cytosine is particularly and even exclusively limited to the genomic region according to SEQ ID NO: 1 for non-classical monocytes as shown using the amplicon according to SEQ ID NO: 1, and in particular in the bisulfite converted sequences according to SEQ ID NO: 2 and/or 3.

The inventors could demonstrate that in the non-classical monocytes the CpG motifs as disclosed are almost completely demethylated (i.e. to more than 70%, preferably 80%, preferably, more than 90% and most preferred more than 95%), whereas the same motifs are completely methylated in all other immune cells.

The differential methylation of the CpG motifs within the aforementioned regions is a valuable tool to identify non-classical monocytes, such as will be required/or at least of some value for identifying and quantifying said cells in autoimmune diseases, transplant rejections, cancer, allergy, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context. The assay allows measurement of non-classical monocytes without purification or any staining procedures.

Another preferred aspect of the method according to the present invention then further comprises a quantification of the relative amount of non-classical monocytes based on comparing relative amounts of said methylation frequency in the 2213 amplicon as analyzed with relative amounts of the methylation frequency in a control gene, such as, for example, GAPDH. Said quantification is thus achieved based on the ratio of the bisulfite convertible DNA to non-convertible DNA in the region within the 2213 amplicon (e.g. of SEQ ID NO: 1) as described and analyzed herein. Most preferred is a quantification of the relative amount of non-classical monocytes is based on an (preferably parallel or simultaneous) analysis of the relative amount of bisulfite convertible DNA of cell-specific region within the 2213 amplicon, and of the relative amount of bisulfite convertible DNA of cell-unspecific genes (preferably designated "control genes" or "control regions", such as, for example, the gene for GAPDH).

In a further preferred embodiment of the method according to the present invention, said analysis of bisulfite convertibility comprises amplification with at least one primer of suitable primer pairs that can be suitably designed based on SEQ ID NO: 1, preferably oligomers according to any of SEQ ID NOs: 4 to 11.

In contrast to FACS and mRNA measurements, using the methods according to the present invention, the measurement(s) and analyses can be done independent of purification, storage—and to quite some extent—also to tissue quality.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, the 2213 amplicon is produced that is a particularly preferred "tool" for performing the method(s) according to the present invention. Consequently, oligomers according to any of SEQ ID NOs: 4 and 5 or 6 and 7 or 9 and 10 or an amplicon as amplified by a primer pair based on SEQ ID NOs: 4 and 5 or 6 and 7 or 9 and 10 as mentioned herein constitute preferred embodiments of the present invention. Thus, the sequences of SEQ ID NOs: 1 to 3 (and, if needed, the complementary sequences thereto) can be used to design primers for amplifications, i.e. serve as "beacons" in the sequence as relevant. Similarly, additional primers and probes can be designed based on the amplicon according to SEQ ID NO: 1. Amplification can take place either in the genomic and/or bisulfite (i.e. "converted") DNA sequence.

The person of skill will furthermore be able to select specific subsets of CpG positions in order to minimize the amount of sites to be analyzed, for example at least one of CpG position selected from a CpG position in an amplicon according to SEQ ID NO: 1, and is preferably selected from CpG positions 30, 89, 123, 169, 206, 242, and 248 in the amplicon No. 2213 according to SEQ ID NO: 1. The positions are numerically counted from the 5'-end of an amplicon as generated and analyzed, and are designated as, e.g., AMP2213:30 in FIG. 1. Preferred are combinations of 3, 4, 5, 6, or 7 positions, the analysis of which produces sufficient data and/or information in order to be informative in the context of the present invention.

The person of skill will furthermore be able to select specific subsets of CpG positions in order to minimize the amount of sites to be analyzed, for example at least one of CpG position 30, 169, 206, and 242 in the amplicon No. 2213 of the specific bisulfite convertible region (SEQ ID NO: 1), or all sites as present on the bisulfite convertible region according to SEQ ID NO: 1. One or more of positions 89, 123 and 248 may be excluded, preferably 123.

In order to analyze the bisulfite convertibility of CpG positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said non-classical monocytes from all major peripheral blood cell types and/or non-blood cells, preferably, but not limited to, from follicular helper T cells, cytotoxic T-cells, granulocytes, classical monocytes, B cells, NK-cells, and T-helper cells, and other cell types derived from other organs than blood.

In yet another preferred embodiment of the method according to the present invention, the sample is selected from a mammalian body fluid, including human blood samples, or a tissue, organ or a sample of leukocytes or a purified or separated fraction of such tissue, organ or leukocytes or a cell type sample. Preferably, said mammal is a mouse, goat, dog, pig, cat, cow rat, monkey or human. The samples can be suitably pooled, if required.

Another preferred aspect of the method according to the present invention then further comprises the step of concluding on the immune status of said mammal based on said B cells. The B cells can be quantified and be used as a benchmark to relatively quantify further detailed subpopulations, or it can be used as a predictive and/or screening and/or diagnostic and/or prognostic and/or adverse events detecting factor, or it can be used to finally detect this population to determine the overall immune activity status.

In yet another preferred embodiment of the methods according to the present invention, the mammal suffers from or is likely to suffer from autoimmune diseases, transplant rejections, infection diseases, cancer, and/or allergy as but not limited to *Trypanosoma cruzi*-infection, Malaria and HIV infection; Hematologic Malignancies as but not limited to chronic Myelogenous Leukemia, Multiple Myeloma, Non Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of non-classical monocytes in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said non-classical monocytes as e.g. a sample for cell transfer into a patient.

Another preferred aspect of the method according to the present invention then relates to a method as above, further comprising formulating said non-classical monocytes as identified for transplantation into a patient. Pharmaceutical preparations for these purposes and methods for their production are performed according to methods known in the art of transplantation medicine.

Another preferred aspect of the method according to the present invention relates to an oligomer according to any of SEQ ID NOs: 4 to 11, or an amplicon according to SEQ ID NOs: 1 to 3.

Yet another preferred aspect of the present invention then relates to a kit for identifying, quantifying, and/or monitoring non-classical monocytes in a mammal based on the analysis of the bisulfite accessibility of CpG positions in the genomic region within the 2213 amplicon, comprising components for performing a method according to the invention as described herein, in particular a kit comprising a) a bisulfite reagent, and b) materials for the analysis of the methylation status of CpG positions selected from the CpG positions in the region according to SEQ ID NO: 1, such as an oligomer selected from the sequences according to SEQ ID NOs: 4 to 11.

The present invention also encompasses the use of oligomers or amplicon or a kit according to the present invention for identifying and/or for monitoring non-classical monocytes in a mammal as described herein.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii) bisulfite convertible (i.e. the "bisulfite convertibility") cytosine encompasses 5-formylcytosine (fC), 5-carboxycytosine (cC), as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

Biomarker Ratio=$a/b$ $a=\Sigma$(C and/or mC and/or hmC and/or fC and/or cC)
$b=\Sigma$(C and/or mC and/or hmC and/or fC and/or cC),
whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

In summary, using the 2213 amplicon as described herein as a marker, the inventors very specifically identified, quantified and particularly differentiated non-classical monocytes, and in their relation to other cell types in a sample, for example to other blood cells.

The invention will now be further described based on the following examples and with reference to the accompanying figures and the sequence listing, without being limited thereto. For the purposes of the present invention, all references as cited herein are incorporated by reference in their entireties.

FIG. 1 shows the analysis of CpG sites on amplicon No. 2213 (SEQ ID NO: 1) according to the invention. The columns in the Figure correspond to the CpG positions in the amplicon as analyzed (e.g. CpG 1, 2, etc.) with the positions indicated, and the horizontal boxes correspond to the cell types as analyzed.

Figure 2A:
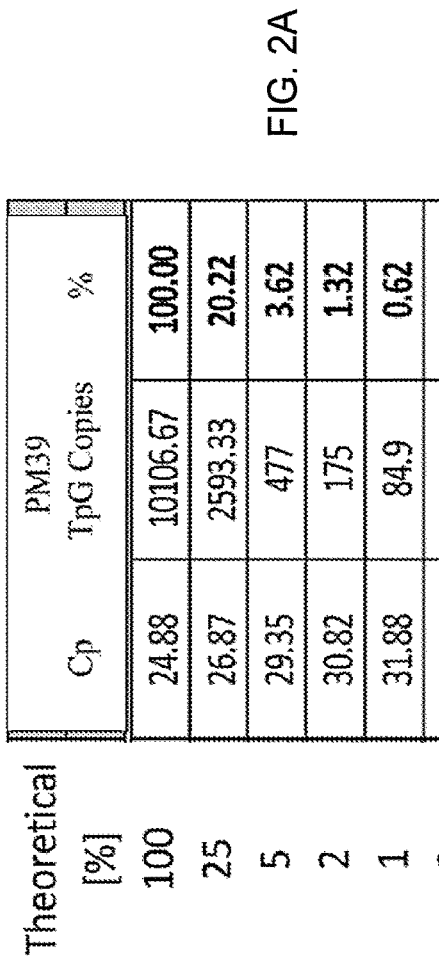
Figure 2B:
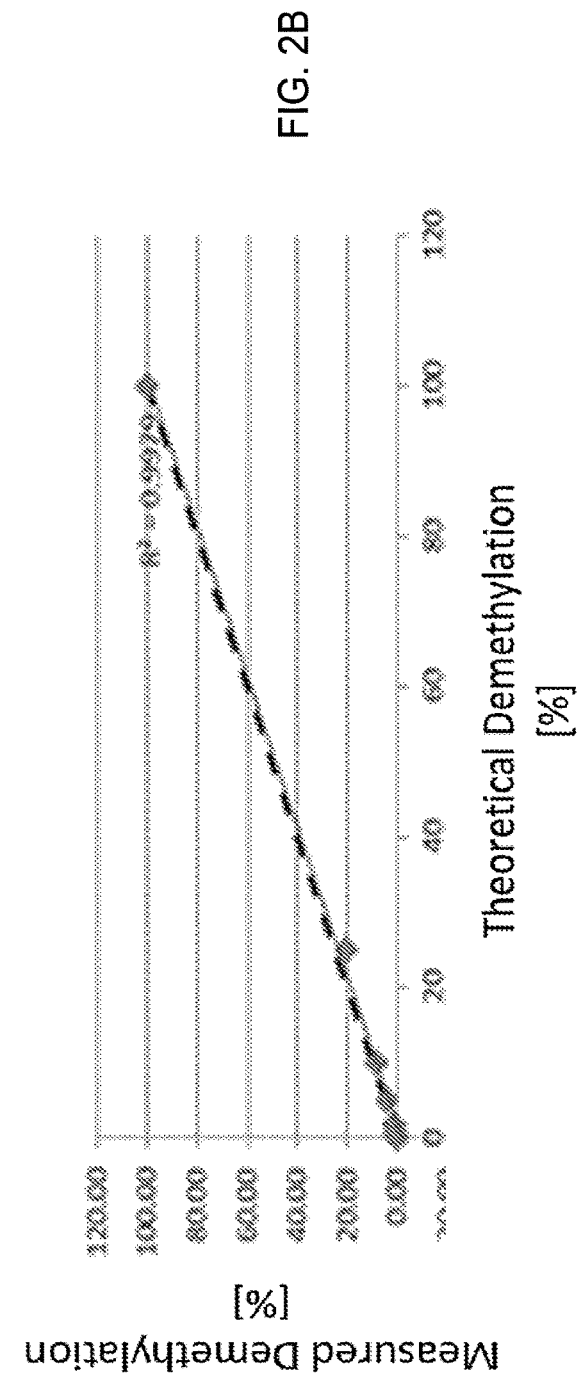

FIG. 2 shows the linearity of the inventive assay as a table (A) and a diagram (B).

SEQ ID NO: 1 shows the genomic sequence of amplicon AMP2213 according to the present invention.

SEQ ID NOs: 2 and 3 show the sequences of bisulfite-converted target-regions of preferred qPCR-assay-systems of the invention, whereby only one of the four possible strands after bisulfite conversion is shown. All four strands are preferred targets for the design of specific assays. The given bisulfite strands named bisulfite strand 2 forward strand (b2f) is merely one preferred target used as the example for primer and probe design. The reverse strand b2r) is used for the complementary primers. The strand b1f and b1r are not shown but preferred applications.

SEQ ID NOs: 4 to 11 show the sequences of specific oligomers (primers and probes) according to the present invention.

EXAMPLES

Example 1

In order to identify non-classical monocytes, qPCR was performed on bisulphite converted samples stemming from the human genomic region according to the following sequence (AMP2213, SEQ ID NO: 1), relevant CpGs are bold and underlined:

CCCTTCCTCTGACTCAGTGGAAGGGCAGGAGAGTGCCCCGAGGAGCTGCC

CACATCCCTGGCTGAGTGCCTCACCCCCAGGGCCTCCACGAGGAGCAGCT

TCCACAGGGTGCCTGTGGGGCTCGTTCCTCTGGATGCTTTTCCCTTTGCT

GTGAATGCCTCTGGGGCACGAATATATGGCCCTTGGGTCTAGGCCTTAGG

GCTTCCGGTGACCAGGATAGGAAGTGTTGCAGGCCCTGCCCCGAGGGCGG

CGCATTAGCTTTTCCCCCACT

For the actual epigenetic profiling of the amplicon region in blood cell subtypes, the immune cell populations as analyzed were as shown in FIG. 1.

The bisulfite-converted target-regions of preferred qPCR-assay-system as developed were:

TpG-specific (SEQ ID No. 2):
(b2F)
CCCTTCCTCTAACTCAATAAAAAAACAAAAAAATACCCCAAAAAACTACC

CACATCCCTAACTAAATACCTCACCCCCAAAACCTCCACAAAAAACAACT

TCCACAAAATACCTATAAAACTCATTCCTCTAAATACTTTTCCCTTTACT

ATAAATACCTCTAAAACACAAATATATAACCCTTAAATCTAAACCTTAAA

ACTTCCAATAACCAAAATAAAAAATATTACAAACCCTACCCCAAAAACAA

CACATTAACTTTTCCCCCACTACTTTCATCTACCCATCTCACCAAATTCC

CpG-specific: (SEQ ID No. 3):
(b2F)
CCCTTCCTCTAACTCAATAAAAAAACAAAAAAATACCCCGAAAAACTACC

CACATCCCTAACTAAATACCTCACCCCCAAAACCTCCACGAAAAACAACT

TCCACAAAATACCTATAAAACTCGTTCCTCTAAATACTTTTCCCTTTACT

ATAAATACCTCTAAAACACGAATATATAACCCTTAAATCTAAACCTTAAA

ACTTCCGATAACCAAAATAAAAAATATTACAAACCCTACCCCGAAAACGA

CGCATTAACTTTTCCCCCACTACTTTCATCTACCCATCTCACCAAATTCC

The following primers and probe were used for the qPCR:

```
Forward amplification primer
2213-fwd
                                          (SEQ ID No. 4)
CCCTTCCTCTAACTCAATAAAA Reverse amplification primer
2213-rev
                                          (SEQ ID No. 5)
AGTGGGGGAAAAGTTAATG Forward primer TpG-specific
2213-TpG-fwd
                                          (SEQ ID No. 6)
CC CTTAAATCTAAACCTTAAAACTTCCA A Reverse primer TpG-specific
2213-TpG-rev
                                          (SEQ ID No. 7)
TAGTGGGGGAAAAGTTAATGTGTT Probe TpG-specific
2213-TpG-pro
                                          (SEQ ID No. 8)
ACAAACCCTACCCCAAAAACAACAC Forward primer CpG-specific
2213-CpG-fwd
                                          (SEQ ID No. 9)
CCTTAAATCTAAACCTTAAAACTTCCGA Reverse primer CpG-specific
2213-CpG-rev
                                          (SEQ ID No. 10)
GTGGAGGAAAAGTTAATGCGTC Probe CpG-specific
2213-CpG-pro
                                          (SEQ ID No. 11)
CAAACCCTACCCCGAAAACGACGC
```

The specificity of the TpG-specific PCR-system was demonstrated using test-templates (plasmid-DNA) as shown in FIG. 2. The cell type specificity (as measured by qPCR) was found as follows:

| Cell type | Description | GAPDH-copies | TpG-copies | Demethylation (%) |
|---|---|---|---|---|
| Granulocytes | CD15+ | 15433.3 | 60.9 | 0.4 |
| Monocytes | CD14+ | 3370.0 | 4.4 | 0.1 |
| Monocytes (II) | CD14+ | 4406.7 | 10.9 | 0.3 |
| Nc Monocytes | CD14 − CD16+ | 3510.0 | 2880.0 | 83.0 |
| Nc Monocytes (II) | CD14 − CD16+ | 3110.0 | 2360.0 | 76.7 |
| cMonocytes | CD14+ | 4216.7 | 7.1 | 0.2 |
| cMonocytes (II) | CD14+ | 4000.0 | 5.3 | 0.1 |
| T helper cells | CD3 + CD4+ | 3893.3 | 10.3 | 0.3 |
| Cytotoxic T cells | CD3 + CD8+ | 1920.0 | 3.2 | 0.2 |
| NK cells | CD56+ | 3306.7 | 5.7 | 0.2 |
| B cells | CD19+ | 3203.3 | 12.4 | 0.4 |

---

The invention claimed is:

1. A method for producing and detecting an amplicon from bisulfite treated DNA comprising the mammalian genomic region of SEQ ID NO: 1 prior to bisulfite treatment, the method comprising
   a) bisulfite treating isolated genomic DNA from a mammalian cell sample to generate bisulfite treated DNA, and
   b) producing the amplicon by amplifying from the bisulfite treated DNA a region comprising the mammalian genomic region of SEQ ID NO: 1 prior to bisulfite treatment, wherein the amplifying is performed with a polymerase chain reaction (PCR), and
   c) detecting the amplicon with a probe comprising the nucleic acid sequence of SEQ ID NO: 8,
   wherein the amplicon comprises CA at CA positions 242 and 248 relative to SEQ ID NO: 2 and one or more CA at a CA position selected from positions 39, 89, 123, 169, and 206 relative to SEQ ID NO: 2.

2. The method according to claim 1, wherein the amplicon comprises two or more CA at CA positions 39, 89, 123, 169, and 206 relative to SEQ ID NO: 2.

3. The method according to claim 1, wherein the CA is detected by a method selected from the group consisting of a methylation specific enzymatic digest, bisulfite sequencing, promoter methylation analysis, CpG island methylation analysis, MSP, HeavyMethyl, MethyLight, Ms-SNuPE, and other methods relying on a detection of amplified DNA.

4. The method according to claim 1, wherein said sample is selected from a body fluid, a blood sample, a tissue sample, an organ sample, a cell type blood sample, or a sample of blood lymphocytes.

5. The method according to claim 1, wherein said method is performed without a step of purifying and/or enriching said cell sample.

6. The method according to claim 1, wherein said cell sample is from a mammal that suffers from or is likely to suffer from autoimmune diseases, transplant rejections, infection diseases, cancer, and/or allergy.

7. The method of claim 1, wherein the method is performed using a kit comprising:
   a) a bisulfite reagent, and
   b) materials for detecting the CA.

8. The method of claim 1, wherein the PCR is performed using an oligomer comprising the sequence of any one of SEQ ID NO: 4 to 5.

9. The method according to claim 1, wherein the amplicon comprises CA at at least three positions selected from positions 39, 89, 123, 169, and 206 relative to SEQ ID NO: 2.

10. The method according to claim 1, wherein the mammalian cell sample is whole blood and/or non-trypsinized tissue.

11. The method of claim 1, wherein the amplicon comprises SEQ ID NO: 2.

12. The method of claim 1, wherein the amplicon comprises CA at positions 39, 89, 123, 169, and 206 of SEQ ID NO: 2.

13. The method of claim 1, wherein the PCR is quantitative PCR (qPCR).

14. The method of claim 8, wherein the PCR is performed using oligomers comprising the sequence of SEQ ID NOs: 6 and 7 or SEQ ID NOs: 4 and 5.

* * * * *